United States Patent [19]

Lieb et al.

[11] Patent Number: 4,622,339
[45] Date of Patent: Nov. 11, 1986

[54] NOVEL NORBORNANE- AND NORBORNENE-CARBOXYLIC ACID AMIDES THROMBOXAN ANTAGONISTS

[75] Inventors: Folker Lieb, Leverkusen; Hermann Oediger, Cologne; Hans-Joachim Kabbe, Leverkusen; Ulrich Niewöhner, Wermelskirchen; Elisabeth Perzborn; Friedel Seuter, both of Wuppertal, all of Fed. Rep. of Germany

[73] Assignee: Bayer Aktiengesellschaft, Leverkusen, Fed. Rep. of Germany

[21] Appl. No.: 691,088

[22] Filed: Jan. 11, 1985

[30] Foreign Application Priority Data

Jan. 20, 1984 [DE] Fed. Rep. of Germany ....... 3401949

[51] Int. Cl.$^4$ .................... A61K 31/44; A61K 31/19; C07C 59/46
[52] U.S. Cl. .................................. 514/563; 514/357; 514/399; 514/400; 514/438; 514/471; 514/511; 514/559; 260/404; 560/37; 560/42; 560/120; 562/442; 562/451; 562/502; 546/337; 548/341; 548/342; 549/76; 549/77; 549/493; 549/496
[58] Field of Search .............. 562/502, 451, 455, 442; 514/563, 510, 511, 357, 399, 400, 438, 471, 559; 560/120, 37, 39, 41, 42; 546/337; 548/341, 342; 549/76, 77, 493, 496; 260/404

[56] References Cited

U.S. PATENT DOCUMENTS

| | | | |
|---|---|---|---|
| 3,378,566 | 4/1968 | MohrbacKer et al. | 546/337 |
| 4,073,933 | 2/1978 | Shimomura et al. | 514/511 |
| 4,368,332 | 1/1983 | Jones et al. | 562/502 |
| 4,430,345 | 2/1984 | Jones et al. | 514/511 |
| 4,438,136 | 3/1984 | Jones et al. | 514/511 |
| 4,458,091 | 7/1984 | Jones et al. | 562/502 |
| 4,473,491 | 9/1984 | Trautmann et al. | 560/120 |

*Primary Examiner*—Natalie Trousof
*Assistant Examiner*—Bruce D. Gray
*Attorney, Agent, or Firm*—Sprung, Horn, Kramer & Woods

[57] ABSTRACT

Norbornane- and norbornene-carboxylic acid amides of the formula

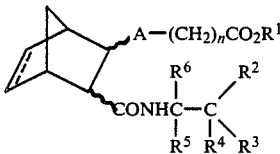

in which

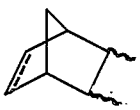

represents the part structure

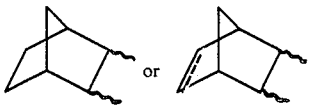

A represents a

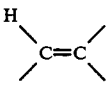

or —CH$_2$—CH$_2$— group,
R$^1$ and R$^2$ each independently is hydrogen or an alkyl radical with 1–6 carbon atoms,
R$^3$ is alkyl or alkenyl which has 1–8 carbon atoms and is optionally substituted by halogen or alkyl with 1 or 2 carbon atoms, cycloalkyl or cycloalkeny with 3 to 7 carbon atoms, an aromatic radical which has 6 or 10 carbon atoms and and is optionally substituted by halogen, by alkyl with 1 or 2 carbon atoms or by halogenoalkyl with 1 or 2 carbon atoms, or is a five-membered or six-membered heteroaromatic radical,
R$^4$ is hydrogen or a hydroxyl group,
R$^5$ and R$^6$ each independently is hydrogen or alkyl with 1 to 4 carbon atoms, and
n is a number from 2 to 6,
and, if R$^1$ is hydrogen, also physiologically acceptable salts thereof, perform as thromboxan antagonists.

12 Claims, No Drawings

NOVEL NORBORNANE- AND NORBORNENE-CARBOXYLIC ACID AMIDES THROMBOXAN ANTAGONISTS

The present invention relates to new norbornane- and norbornene-carboxylic acid amides, processes for their preparation and the use of norbornane- and norbornene-carboxylic acid amides as medicaments, in particular as antithrombotics, antiatherosclerotics and antiischaemic agents.

Thrombosis and arteriosclerotic vascular changes are chiefly controlled by the interaction of two metabolites of arachidonic acid, that is to say by thromboxan $A_2$ ($TXA_2$) and by prostacyclin ($PGI_2$). $TXA_2$ has an aggregating effect on the blood platelets, and $PGI_2$ has an anti-aggregating action. Furthermore, $TXA_2$ has a vasoconstricting action and $PGI_2$ has a vasodilating action.

In a number of thrombo-embolic and ischaemic diseases, hyperaggregability of the platelets or an increased platelet consumption leads to an increased thromboxan synthesis, so that the equilibrium between $TXA_2$ and $PGI_2$ is disturbed. It is therefore desirable, for the therapy and prophylaxis of thrombo-embolic and ischaemic diseases, to inhibit the action of thromboxan and thus to increase the protective characteristic of the $PGI_2$.

It has now been found, surprisingly, that certain norbornane- and norbornene-carboxylic acid amides have a specific and powerful antagonistic action in respect of thromboxan $A_2$.

Thromboxan-antagonistic and platelet aggregation-inhibiting norbornane- and norbornene-carboxylic acid amides of the general formula (I)

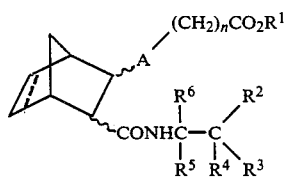

(I)

in which

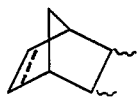

represents the part structures

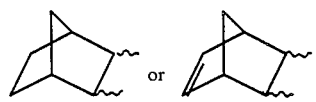

A represents a

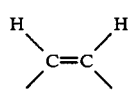

or —CH$_2$CH$_2$— group, $R^1$ and $R^2$ represent hydrogen or an alkyl radical with 1–6 carbon atoms, $R^3$ represents alkyl or alkenyl which has 1–8 carbon atoms and is optionally substituted by halogen or alkyl with 1 or 2 carbon atoms, or represents cycloalkyl or cycloalkenyl with 3 to 7 carbon atoms, or an aromatic radical which has 6 or 10 carbon atoms and is optionally substituted by halogen, alkyl with 1 or 2 carbon atoms or halogenoalkyl with 1 or 2 carbon atoms, or represents a five-membered or six-membered heteroaromatic radical, $R^4$ represents hydrogen or a hydroxyl group, $R^5$ and $R^6$ are identical or different and represent hydrogen or alkyl and n represents a number from 2 to 6, and, if $R^1$ denotes hydrogen, also physiologically acceptable salts thereof, have been found.

The symbol ~ denotes that the side chains on the bicyclic radical are in the exo- or endo-position.

Preferred compounds are those in which $R_1$ represents hydrogen, methyl or ethyl, those in which n represents 2–4, those in which $R^4$ represents hydrogen or a hydroxyl group and those in which $R^5$ and $R^6$ represent hydrogen.

The new norbornane- and norbornene-carboxylic acid amides can be in the form of enantiomers, enantiomer pairs and diastereomer pairs.

It has furthermore been found that the norbornane- and norbornene-carboxylic acid amides of the general formula (I) are obtained by a process in which, in accordance with equation I, a lactone of the general formula (II)

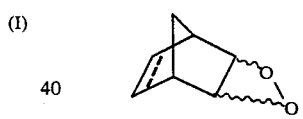

(II)

in which

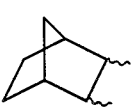

represents the part structure

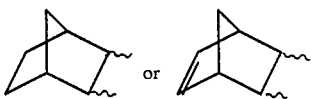

is reduced with an organoaluminum hydride to give a lactol of the general formula (III)

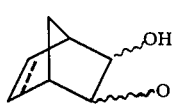

(III)

in which

has the above meaning,
and the lactol thus obtained is reacted with a phosphonium salt of the general formula (IV)

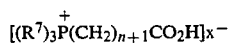   (IV)

in which
R$^7$ represents an aryl radical,
X represents a halogen and
n represents a number between 2 and 6,
in the presence of a base, to give an acid of the general formula (V)

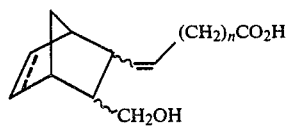   (V)

in which

and n have the above meanings, and this acid is then reacted with an alcohol of the general formula (VI)

R$^8$OH   (VI)

in which
R$^8$ represents an alkyl radical with 1 to 6 carbon atoms,
to give the ester of the general formula (VII)

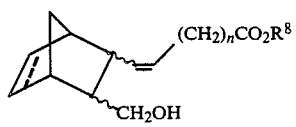   (VII)

in which

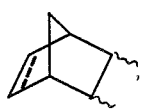

n and R$^8$ have the abovementioned meanings,
and, if A in the general formula (I) represents

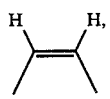

this ester is oxidized to give an acid of the general formula (VIII)

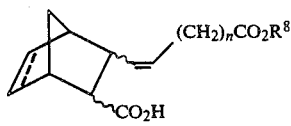   (VIII)

in which

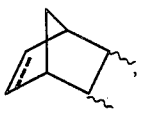

n and R$^8$ have the above meanings, and the acid thus obtained is reacted, if appropriate with conversion into an activated ester, with an amine of the general formula (IX)

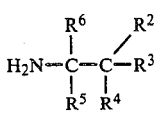   (IX)

in which
R$^2$ represents hydrogen or an alkyl radical with 1–6 carbon atoms,
R$^3$ represents alkyl or alkenyl which has 1 to 8 carbon atoms and is optionally substituted by halogen or alkyl with 1 or 2 carbon atoms, or represents cycloalkyl or cycloalkenyl with 3 to 7 carbon atoms, or an aromatic radical which has 6 or 10 carbon atoms and is optionally substituted by halogen, alkyl with 1 or 2 carbon atoms or halogenoalkyl with 1 or 2 carbon atoms, or represents a five-membered or six-membered heteroaromatic radical,
R$^4$ represents hydrogen or a hydroxyl group and
R$^5$ and R$^6$ are identical or different and represent hydrogen or alkyl with 1 to 4 carbon atoms,
to give the amide-esters (I) or, if appropriate, with subsequent hydrolysis, to give the amide-acids (I), or, if A in the general formula (I) represents a —CH$_2$CH$_2$— group and

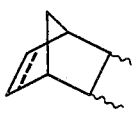

represents the part structure

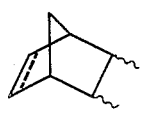

the unsaturated ester of the general formula (VII) is hydrogenated catalytically to give the ester of the general formula (X)

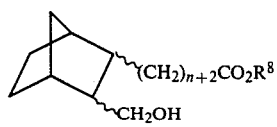

in which

R⁸ and n have the abovementioned meanings,
this ester is converted into an acid of the general formula (XI)

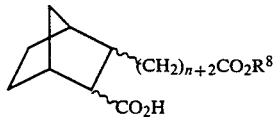

in which

R⁸ and n have the above meanings,
and the resulting acid (XI) is reacted, if appropriate with conversion into an activated ester, with an amine of the general formula (IX) to give the amide-esters (I) or, if appropriate, with subsequent hydrolysis, to give the amide-acids (I).

If hexahydro-4,7-methano-isobenzofuran-1(3H)-one is used as the starting substance and sodium bis(2-methoxy-ethoxy)-dihydrido-aluminate is used as the reducing agent in the first stage of the process, 4-carboxybutyl-triphenylphosphonium bromide and, as the base, sodium hydride in dimethylsulphoxide are used in the second stage, methanol in the presence of a strong acid is used in the third stage, pyridinium dichromate is used in the fourth stage, 2-hydroxy-2-phenyl-propylamine and dicyclohexylcarbodiimide are used in the fifth stage, sodium hydroxide solution is used in the sixth stage and, in one variant of the process according to the invention, hydrogen is used as the hydrogenating agent and palladium-on-charcoal is used as the catalyst, pyridinium dichromate is used as the oxidizing agent in the subsequent stage and 2-(m-chlorophenyl)-2-hydroxyethylamine is used as the amine in a further subsequent stage, the courses of the reactions can be represented by the following equation:

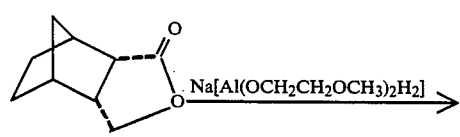

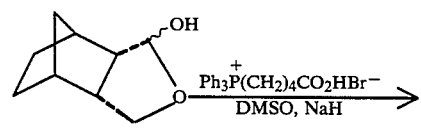

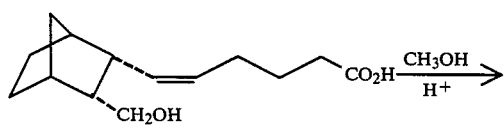

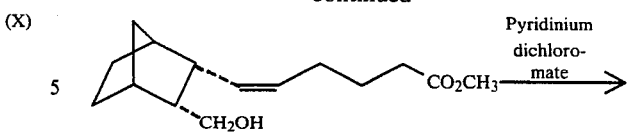

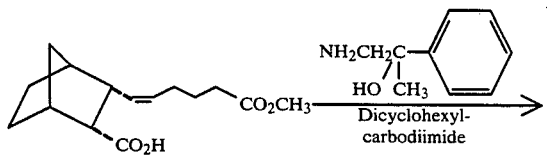

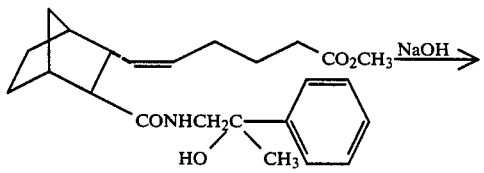

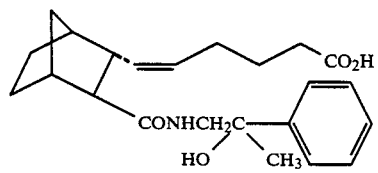

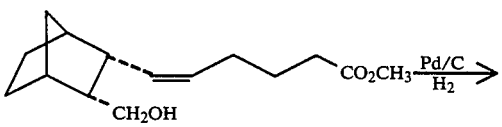

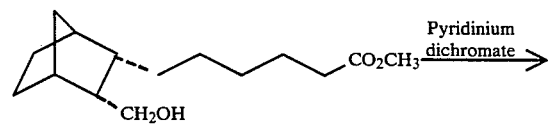

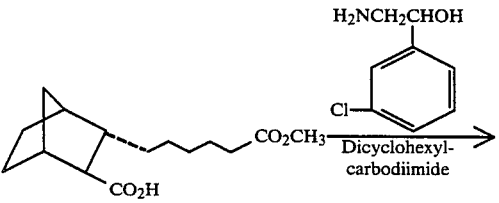

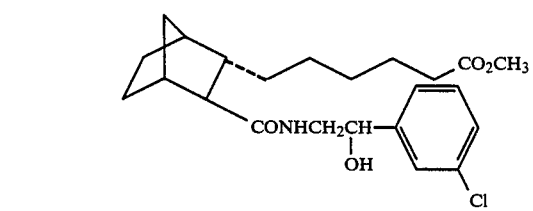

The lactones of the general formula (II) used as starting substances are known.

Hexahydro-4,7-methano-iso-benzofuran-1(3H)-one; and tetrahydro-4,7-methano-iso-benzofuran-1(3H)-one; (J. C. S. Perkin I 1981, page 3101, Tetrahedron Letters 1982, page 539).

According to equation I, the lactones (II) are reduced with alkali metal alkoxy-hydridoaluminates, for example sodium bis-(2-methoxy-ethoxy)-dihydrido-aluminate or sodium ethoxy-bis(2-methoxy-ethoxy)-hydrido-aluminate, or with dialkylaluminum hydride, for example diisobutyl-aluminum hydride, in the first stage of the process.

Sodium bis-(2-methoxy-ethoxy)-dihydrido-aluminate is a particularly suitable reducing agent.

Possible diluents are inert hydrocarbons, such as toluene, and ethers, such as tetrahydrofuran or diethylene glycol dimethyl ether. Toluene is particularly suitable.

The reaction temperatures are between $-78°$ and $-40°$ C., preferably between $-70°$ and $-78°$ C.

The reaction time depends on the reaction temperature and is between 4 and 10 hours. In general, 1 mole of the lactone (II) is reacted with at least one hydride equivalent of the reducing agent. An excess does no harm.

In a second stage of the process according to the invention, the lactol of the general formula (III) is reacted with a phosphonium salt of the general formula (IV) in the presence of a base in accordance with equation 1.

The phosphonium salts used as starting substances are known (J. Am. Chem. Soc. 1969, Volume 91, page 5675).

In formula (IV), n preferably represents 2 to 4, $R^7$ represents phenyl and X represents Cl, Br or I, in particular Br or Cl.

The following compounds may be mentioned as examples: 3-carboxy-propyl-triphenylphosphonium bromide, 4-carboxy-butyltriphenylphosphonium bromide, 4-carboxybutyl-triphenylphosphonium chloride and 5-carboxy-pentyltriphenylphosphonium bromide.

Suitable bases are alkali metal hydrides, such as sodium hydride or potassium hydride, preferably sodium hydride.

Dimethylsulphoxide is a possible solvent.

The reaction temperature is initially in a range between 30° and 90° C., preferably from 60° to 70° C. (preparation of the sodium salt of dimethylsulphoxide) and subsequently in a temperature range between 10° and 40° C., preferably 15° and 20° C.

The reaction time depends on the temperature and is in general between 1 and 6 hours.

In general, 1 mole of the lactol (III) is reacted with 1.0 to 3.0 moles, preferably 2.0 to 3.0 moles, of a phosphonium salt of the general formula (IV), which has initially been reacted with 2.0 to 6.0 moles, preferably with 4.0 to 6.0 moles, of base.

In a third stage of the process, the acid of the general formula (V) is reacted with an alcohol of the general formula (VI) in accordance with the equation. Suitable alcohols are lower alcohols, such as methanol, ethanol and propanol, in particular methanol and ethanol.

The reaction is carried out with addition of a second acid. Acids which are suitable for this are inorganic acids, such as hydrochloric acid, sulphuric acid and phosphoric acid, preferably sulphuric acid, or organic acids, such as methanesulphonic acid, benzenesulphonic acid or p-toluenesulphonic acid, preferably p-toluenesulphonic acid.

An excess of alcohol or chlorinated hydrocarbons, such as methylene chloride, carbon tetrachloride, 1,2-dichloroethane or trichloroethylene, preferably methylene chloride or carbon tetrachloride or a combination of the two diluents, is suitable as the diluent.

The reaction temperatures can be varied within a substantial range. In general, the reaction is carried out between 60° and 97° C., preferably preferred is reflux temperature.

The reaction time depends on the temperature and is in general between 4 and 20 hours.

In general, 1 mole of the acid (V) is reacted with 1.5 to 6 moles of alcohol (IV) with addition of 0.1 to 0.2 mole of acid. An excess of alcohol does no harm.

According to equation I, a compound of the general formula (VII) is oxidized with hexavalent chromium in a fourth stage of the process according to the invention.

Jones reagent, that is to say acidified chromium trioxide, is a suitable oxidizing agent (J. Chem. Soc. 1947, page 39). Acetone is a suitable diluent.

The reaction temperature is between $-70°$ and $+20°$ C., advantageously $-25°$ to 0° C. The reaction time depends on the temperature and is in general between 2 and 4 hours.

Usually, 1 mole of the alcohol (VII) is reacted with the stoichiometrically calculated amount, or with an up to 8-molar excess, of oxidizing agent.

Pyridinium dichromate is another suitable oxidizing agent (Tetrahedron Letters 1979, page 399).

Dimethylformamide is a suitable diluent. The reaction temperature is between 0° and 40° C., preferably between 10° and 25° C. The reaction time depends on the temperature and is in general between 8 and 24 hours.

In general, 1 mole of the alcohol (VII) is reacted with 0.5 to 5 moles, preferably with 2 to 4 moles, of pyridinium dichromate.

In the fifth stage of the process, an acid of the general formula (VIII) is first reacted with 1-hydroxybenzotriazole, with addition of a dehydrating agent, and then with an amine of the general formula (IX), as the hydrochloride, with addition of a base.

1-Hydroxybenzotriazole is known (J. prakt. Chem. Volume 111, page 272 (1925)).

The amines of the general formula (IX) are known or can be prepared by known processes. (J. Org. Chem. Volume 25, 257 (1960); J. Amer. Chem. Soc. volume 73, page 2359 (1951); and J. Org. Chem. Volume 39, page 914 (1974)).

Preferably, in formula (IX), $R^2$ represents hydrogen or alkyl with 1 to 4 carbon atoms, in particular hydrogen or methyl, $R^3$ represents alkyl or alkenyl with 1 to 6 carbon atoms, in particular propyl, butyl or pentyl, or represents cycloalkyl or cycloalkenyl with 5 or 6 carbon atoms, in particular cyclopentyl, cyclohexyl or cyclohexenyl, or represents phenyl or phenyl which is substituted by halogen, preferably fluorine or chlorine, or by alkyl, preferably methyl or trifluoromethyl, in particular phenyl or phenyl which is substituted by chlorine or trifluoromethyl, or represents heteroaryl, such as pyridyl, imidazolyl, furyl or thienyl, in particular pyridyl or imidazolyl, $R^4$ represents hydrogen or a hydroxyl group and $R^5$ and $R^6$ represent hydrogen or alkyl with 1-3 carbon atoms, in particular hydrogen.

The following compounds may be mentioned as examples: 2-hydroxyhexylamine, 2-hydroxy-2-(cyclohex-3-en-yl)ethylamine, 2-hydroxy-2-methyl-pentylamine, 2-m-chlorophenyl-2-hydroxy-ethylamine, 2-hydroxy-2-phenylpropylamine, 2-phenyl-propylamine, 2-methylpentylamine, 2-m-chlorophenylethylamine and 2-m-trifluoromethylphenylethylamine.

Possible diluents are all the inert organic solvents. These include, preferably, ethers, such as tetrahydrofuran, dioxane, diethylene glycol dimethyl ether or triethylene glycol dimethyl ether, in particular tetrahydrofuran or diethylene glycol dimethyl ether.

Suitable dehydrating agents are carbodiimides, in particular cyclohexylcarbodiimide.

Tertiary amines, such as triethylamine, N-ethylmorpholine, dimethylaniline, 1-methylpiperidine and dimethylcyclohexylamine, in particular triethylamine and N-ethylmorpholine, are used as the base.

The reaction temperatures can be varied within a substantial range. In general, the reaction is carried out between −10° and 40° C., preferably between −5° and 30° C.

The reaction time depends on the temperature and is between 2 and 6 hours.

In carrying out the process according to the invention, 1 mole of the acid (VIII) is reacted with 1 mole of N-hydroxybenzotriazole, with addition of 1.0 to 1.2 moles, preferably 1.0 to 1.1 moles, of cyclohexylcarbodiimide, and then with 1.0 to 1.1 moles, in particular with 1.0 to 1.05 moles, of amine of the general formula (IX).

In the sixth stage of the process, the amide-esters of the general formula (I) are hydrolyzed to the amide-acids of the general formula (I).

Possible diluents are aqueous alcohols, such as methanol, ethanol or propanol, preferably methanol.

Alkali metal hydroxides and alkali metal carbonates can be used as the bases. Particularly suitable bases which may be mentioned specifically are: sodium hydroxide and potassium hydroxide.

The reaction temperatures are between 0° and 40° C., preferably between 10° and 30° C.

The reaction time depends on the reaction temperature and is between 12 and 48 hours.

In general, 1 mole of the amide-ester (I) is reacted with 1.0 to 3.0 moles, preferably with 1.0 to 1.5 moles, of base.

In one variant of the process according to the invention, as described in equation I, the unsaturated ester (VII) is hydrogenated.

Metal catalysts, preferably platinum, palladium or Raney nickel, in particular palladium, are used as the catalysts.

The choice of diluent depends on the catalyst. If palladium-on-charcoal is used, alcohols, such as methanol, ethanol and propanol, in particular methanol and ethanol, are suitable.

The reaction temperature can be varied within wide limits. In general, the reaction is carried out at 20° to 100° C., preferably at 40° to 70° C.

The reaction time depends on the temperature and is between 1 and 4 hours.

The reaction is carried out under increased pressure. In general, it is carried out under pressures between 1.5 and 35 bar, preferably between 10 and 30 bar.

In carrying out the process according to the invention, 1 mole of the unsaturated ester (VII) is reacted with an excess of hydrogen in the presence of 1 to 100 mmol, preferably 1 to 60 mmol, of palladium-on-charcoal.

In a further stage of the process according to the invention, the ester (X) is oxidized with hexavalent chromium to give the acid (XI), as described in the fourth stage of the process.

Thereafter, analogously to the fifth and sixth stage of the process according to the invention, the acid of the general formula (XI) is reacted with amines of the general formula (IX) to give the amide-esters (I) or, if appropriate, after subsequent hydrolysis, to give the amide-acids of the general formula (I).

The following active compounds may be mentioned specifically as being suitable for the medicaments according to the invention: methyl 6-[3-(N-2-hydroxyhexyl)-carbamyl-bicyclo[2.2.1]hept-2-yl]-hex-5-enoate, methyl 6-[3-(N-2-(cyclohex-3-en-yl)-2-hydroxy-ethyl)-carbamyl-bicyclo[2.2.1]hept-2-yl]-hex-5-enoate, methyl 6-[3-(N-2-hydroxy-2-methyl-pentyl)-carbamyl-bicyclo[2.2.1]hept-2-yl]-hex-5-enoate, methyl 6-[3-(N-2-m-chlorophenyl-2-hydroxyethyl)-carbamyl-bicyclo[2.2.1]hept-2-yl]-hex-5-enoate, methyl 6-[3-(N-2-hydroxy-2-phenyl-propyl)-carbamyl-bicyclo[2.2.1]hept-2-yl]-hex-5-enoate, methyl 6-[3-(N-2-phenyl-propyl)-carbamyl-bicyclo[2.2.1]hept-2-yl]-hex-5-enoate, methyl 6-[3-(N-2-methyl-pentyl)-carbamyl-bicyclo[2.2.1]hept-2-yl]-hex-5-enoate, methyl 6-[3-(N-2-m-chlorophenyl-ethyl)-carbamyl-bicyclo[2.2.1]hept-2-yl]-hex-5-enoate, methyl 6-[3-(N-2-hydroxy-hexyl)-carbamyl-bicyclo[2.2.1]hept-5-en-2-yl]-hex-5-enoate, methyl 6-[3-(N-2-hydroxy-2-methyl-pentyl)-carbamyl-bicyclo[2.2.1]hept-5-en-2-yl]-hex-5-enoate, methyl 6-[3-(N-2-m-chlorophenyl-2-hydroxy-ethyl)carbamyl-bicyclo[2.2.1]hept-5-en-2-yl]-hex-5-enoate, methyl 6-[3-(N-2-m-trifluoromethylphenyl-2-hydroxy-ethyl)-carbamyl-bicyclo[2.2.1]hept-5-en-2-yl]-hex-5-enoate, 6-[3-(N-2-hydroxyhexyl)-carbamyl-bicyclo[2.2.1]-hept-2-yl]-hex-5-enoic acid, 6-[3-(N-2-hydroxy-2-(cyclohex-3-en-yl)-ethyl)-carbamyl-bicyclo[2.2.1]hept-2-yl]-hex-5-enoic acid, 6-[3-(N-2-hydroxy-2-methyl-pentyl)-carbamyl-bicyclo[2.2.1]hept-2-yl]-hex-5-enoic acid, 6-[3-(N-2-m-chlorophenyl-2-hydroxy-ethyl)-carbamyl-bicyclo[2.2.1]hept-2-yl]-hex-5-enoic acid, 6-[3-(N-2-hydroxy-2-phenyl-propyl)-carbamyl-bicyclo[2.2.1]hept-2-yl]-hex-5-enoic acid, 6-[3-(N-2-phenyl-propyl)-carbamyl-bicyclo[2.2.1]hept-2-yl]-hex-5-enoic acid, 6-[3-(N-2-methyl-pentyl)-carbamyl-bicyclo[2.2.1]hept-2-yl]-hex-5-enoic acid, 6-[3-(N-2-m-chlorophenyl-ethyl)-carbamyl-bicyclo[2.2.1]hept-2-yl]-hex-5-enoic acid, 6-[3-(N-2-hydroxy-hexyl)-carbamyl-bicyclo[2.2.1]hept-5-en-2-yl]-hex-5-enoic acid, 6-[3-(N-2-hydroxy-2-methyl-pentyl)-carbamyl-bicyclo[2.2.1]hept-5-en-2-yl]-hex-5-enoic acid, 6-[3-(N-2-m-chlorophenyl-2-hydroxyethyl)-carbamyl-bicyclo[2.2.1]hept-5-en-2-yl]-hex-5-enoic acid, 6-[3-(N-2-m-trifluoromethylphenyl-2-hydroxy-ethyl)-carbamyl-bicyclo[2.2.1]hept-5-en-2-yl]-hex-5-enoic acid, methyl 6-[3-(N-2-phenyl-propyl)-carbamyl-bicyclo[2.2.1]-hept-2-yl]-hexanoate, methyl 6-[3-(N-2-methyl-pentyl)-carbamyl-bicyclo[2.2.1]hept-2-yl]-hexanoate, methyl 6-[3-(N-2-m-chlorophenyl-ethyl)-carbamyl-bicyclo[2.2.1]hept-2-yl]-hexanoate, 6-[3-(N-2-phenyl-propyl)-carbamyl-bicyclo[2.2.1]hept-2-yl]-hexanoic acid, 6-[3-(N-2-methyl-pentyl)-carbamyl-bicyclo[2.2.1]hept-2-yl]-hexanoic acid and 6-[3-(N-2-m-chlorophenyl-ethyl)-carbamyl-bicyclo[2.2.1]hept-2-yl]-hexanoic acid.

Possible formulation forms are the usual galenical forms of administration, for example, creams, tablets, pills, capsules, suppositories, emulsions and infusion and injection solutions. These formulation forms are prepared by methods which are known per se, using customary auxiliaries and excipients.

The medicaments thus prepared are used according to requirements, for example by local, parenteral or oral administration.

Formulations which contain the compounds according to the invention in concentrations of about 0.1 to 10% by weight are particularly suitable. Aqueous solutions, which are buffered, if appropriate, at a pH value of 6 to 8, are particularly preferred.

The dosage of norbornane- or norbornene-carboxylic acid amides in the medicaments according to the invention is preferably in a range from 0.05 to 100 mg/kg, in particular from 0.1 to 20 mg/kg of body weight.

The norbornane- or norbornene-carboxylic acid amides contained in the medicaments according to the invention are suitable as thromboxan antagonists and platelet aggregation inhibitors for preventing and treating thrombo-embolic diseases in the venous and arterial region and postoperative thromboses and for promoting the permeability of surgically grafted vascular transplants. The new compounds according to the invention are also suitable for preventing and treating arteriosclerosis, ischaemic diseases, in particular cardiac infarctions, transitory ischaemic attacks (TIA) and apoplexy, angina pectoris, sudden heart death, disorders in peripheral circulation, migraines and diseases of the respiratory tract, such as asthma, bronchitis, bronchiectasis, pneumonia and emphysema.

METHOD

In vitro inhibition of platelet aggregation

Blood from healthy donors who have not taken any medicament for at least 14 days is used for the in vitro determination of the platelet aggregation-inhibiting action. The blood is taken up in 3.8% strength sodium citrate solution. Platelet-rich plasma (PRP) is obtained by centrifugation at 150 g at room temperature for 20 minutes (Jürgens/Beller: Klinische Methoden der Blutgerinnungsanalyse (Clincal Methods of Blood Coagulation Analysis); Thieme Verlag, Stuttgart 1959). The platelet aggregation is determined by the turbidometric method (Born, G.V.R.: J. Physiol. 162, 67, 1962) in an aggregometer at 37° C. For this, the PRP is incubated with the test substance at 37° C. and aggregation is then induced by addition of a collagen suspension. The minimum effective concentration of active compound (MEC) which inhibits platelet aggregation in the corresponding PRP samples is given for the in vitro experiments.

The aggregation-inhibiting action can be attributed to a direct interaction with the thromboxan/PGH$_2$ receptor. To determine this specific thromboxan-antagonistic action, the platelet aggregation is induced by the stable PGH$_2$ analogue 9,11-epoxymethano-PGH$_2$ (U 44069), which acts as a thromboxan agonist (Bundy, G. L.: Tetrahedron Lett. 1975, 1957-1960). The platelet aggregation is measured by a process analogous to that described for collagen-induced platelet aggregation.

Ex vivo inhibition of platelet aggregation

For the ex vivo investigations, the active substance was administered orally in a Tylose suspension to the animals. After 90 minutes, the animals were exsanguinated and the PRP was obtained by means of centrifugation. The inhibition of aggregation is measured by a process analogous to that described for the in vitro experiments, but without preincubation of the samples.

Results

The inhibition of platelet aggregation (in vitro) induced by collagen or U 44069 and the inhibition of platelet aggregation (ex vivo) was determined on the compounds mentioned in Table 1.

The norbornane- and norbornene-carboxylic acid amides (see, for example, compound 20, 23, 24 or 30) inhibit both collagen-induced and U 44069-induced platelet aggregation more powerfully than AH 19437, a thromboxan antagonist which is known from the literature (Geisow, H. P., Hornby, E. J., McCabe, P. J., Brit. J. Pharmacol. 73, 219 P, 1981).

The norbornane- and norbornene-carboxylic acid amides (see, for example, compound 23 or 30) are more powerful inhibitors of collagen-induced aggregation than SQ 26 536 (Harris, D. N., Phillips, M. B., Mishel, I. M., Goldenberg H. J., Heikes, J. E., Sprague, P. W., Antonaccio, M. J., Prostaglandins 22, 295-307, 1981).

TABLE 1

| Compound according to Example No. | in vitro inhibition of platelet aggregation minimum effective concentration (g/ml) | | ex vivo inhibition of platelet aggregation | |
|---|---|---|---|---|
| | collagen-induced | U 44069-induced | Dose (mg/kg) | Inhibition (90) |
| 10 | $1 \times 10^{-5}$–$3 \times 10^{-6}$ | — | 100 | >50 |
| 11 | $3 \times 10^{-6}$–$1 \times 10^{-6}$ | $1 \times 10^{-5}$–$3 \times 10^{-6}$ | | |
| 20 | $3 \times 10^{-6}$–$1 \times 10^{-6}$ | $3 \times 10^{-6}$–$1 \times 10^{-6}$ | 100 | >50 |
| 21 | $3 \times 10^{-6}$–$1 \times 10^{-6}$ | $1 \times 10^{-5}$–$3 \times 10^{-6}$ | 100 | >50 |
| | | | 30 | >50 |
| | | | 10 | ~50 |
| 22 | $3 \times 10^{-6}$–$1 \times 10^{-6}$ | $1 \times 10^{-5}$–$3 \times 10^{-6}$ | 100 | ~50 |
| 23 | $3 \times 10^{-6}$–$1 \times 10^{-6}$ | $1 \times 10^{-6}$–$3 \times 10^{-7}$ | 100 | >50 |
| 24 | $1 \times 10^{-6}$–$3 \times 10^{-7}$ | $3 \times 10^{-6}$–$1 \times 10^{-6}$ | 100 | >50 |
| | | | 30 | <50 |
| 29 | $1 \times 10^{-5}$–$3 \times 10^{-6}$ | $1 \times 10^{-5}$–$3 \times 10^{-6}$ | 100 | ~50 |
| 30 | $1 \times 10^{-6}$–$3 \times 10^{-7}$ | $1 \times 10^{-6}$–$3 \times 10^{-7}$ | 100 | >50 |
| | | | 30 | >50 |
| | | | 10 | <50 |

EXAMPLE 1

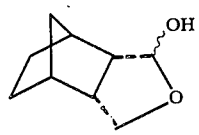

1-Hydroxy-octahydro-4,7-methano-iso-benzofuran 30.4 g (0.2 mole) of hexahydro-4,7-methano-iso-benzofuran-1(3H)-one are introduced into 800 ml of absolute toluene, under an inert gas, and 84.8 ml (0.3 mole) of sodium bis-(2-methoxy-ethoxy)-dihydridoaluminate (70% strength solution in toluene), diluted with 200 ml of absolute toluene, are allowed to run in at −70° to −78° C. The mixture is stirred at −70° to −78° C. for 6 hours. Thereafter, 580 ml of 50% strength aqueous methanol are added dropwise at −70° C. and the mixture is subsequently stirred at 20° C. for 15 minutes and diluted with 400 ml of saturated aqueous sodium chloride solution. The organic phase is separated off and the aqueous phase is extracted with ethyl acetate. The organic phases are combined, washed with saturated aqueous sodium chloride solution and dried over sodium sulphate and the solvent is evaporated off in vacuo. 30.1 g (98% yield) of 1-hydroxyoctahydro-4,7-methano-iso-benzofuran are obtained in this manner.

$R_F$=0.38 [methylene chloride/methanol (95:5)/silica gel].

EXAMPLE 2

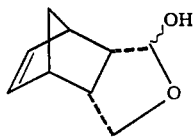

1-Hydroxy-hexahydro-4,7-methano-iso-benzofuran 29.8 g (98% yield) of 1-hydroxy-hexahydro-4,7-methano-iso-benzofuran are obtained analogously to Example 1 from 30.0 g (0.2 mole) of tetrahydro-4,7-methano-iso-benzofuran-1(3H)-one.

$^{13}$C-NMR(CDCl$_3$): δ = 100.278 ppm

EXAMPLE 3

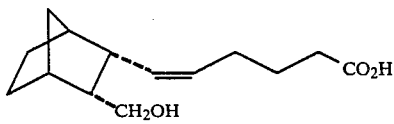

6-(3-Hydroxymethyl-bicyclo[2.2.1]hept-2-yl)-hex-5-enoic acid 12 g (0.4 mole) of 80% strength NaH are added to 240 ml of absolute dimethylsulphoxide under an inert gas, and the mixture is warmed at 60° to 70° C. until the evolution of hydrogen has ended. Thereafter, 88.4 g (0.2 mole) of 4-carboxybutyl-triphenyl-phosphonium bromide in 200 ml of absolute dimethylsulphoxide are added at 15° to 16° C. After the mixture has been subsequently stirred for 10 minutes, 15.4 g (0.1 mole) of 1-hydroxyoctahydro-4,7-methano-iso-benzofuran in 50 ml of absolute dimethylsulphoxide are allowed to run in and the mixture is stirred at 20° C. for 3 hours. 20 ml of water are then added, the solvent is distilled off in vacuo and the evaporation residue is partitioned between 200 ml of water and 4×400 ml of diethyl ether. The aqueous phase is brought to pH 3.5 with 5N hydrochloric acid and the precipitate which deposits is separated off and washed 3, times with 200 ml of diethyl ether. The aqueous phase which remains is saturated with sodium chloride and extracted 5 times with 200 ml of diethyl ether. After the combined ethereal extracts have been dried, the solvent is evaporated off in vacuo and the residue is chromatographed on silica gel using methylene chloride/tetrahydrofuran/acetic acid (10:1:0.5). 30.9 g of 6-(3-hydroxymethylbicyclo[2.2.1]hept-2-yl)-hex-5-enoic acid are obtained in this manner (65% yield).

$^1$H-NMR (CDCl$_3$): δ = 5.00–5.39 ppm (multiplet).

EXAMPLE 4

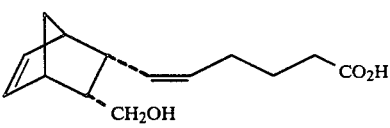

6-(3-Hydroxymethyl-bicyclo[2.2.1]hept-5-en-2-yl)-hex-5-enoic acid 6-(3-Hydroxymethyl-bicyclo[2.2.1]hept-5-en-2-yl)hex-5-enoic acid is obtained analogously to Example 3 (yield: 66%).

$^1$H-NMR (CDCl$_3$): δ = 5.13–5.50 (multiplet) and 5.89–6.27 (multiplet) ppm.

EXAMPLE 5

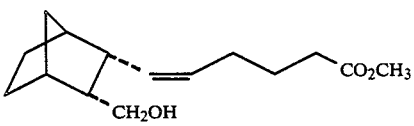

Methyl 6-(3-hydroxymethyl-bicyclo[2.2.1]hept-2-yl)-hex-5-enoate 65.7 g (0.28 mole) of 6-(3-hydroxymethyl-bicyclo[2.2.1]hept-2-yl)-hex-5-enoic acid are heated under reflux in 220 ml of methanol and 600 ml of carbon tetrachloride with the addition of 6.0 g (0.03 mole) of p-toluenesulphonic acid, for 16 hours. The mixture is then washed 3 times with 500 ml of saturated aqueous sodium bicarbonate solution and twice with 500 ml of saturated aqueous sodium chloride solution. The mixture is dried over sodium sulphate and the solvents are then evaporated off in vacuo. 66.4 g (yield: 95%) of methyl 6-(3-hydroxymethyl-bicyclo-[2.2.1]hept-2-yl)-hex-5-enoate are obtained.

$^1$H-NMR(CDCl$_3$): δ = 3.62 ppm (singlet).

EXAMPLE 6

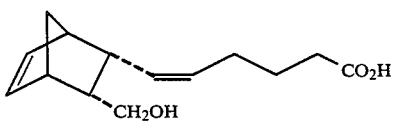

Methyl 6-(3-hydroxymethyl-bicyclo[2.2.1]hept-5-en-2-yl)-hex-5-enoate

Methyl 6-(3-hydroxymethyl-bicyclo[2.2.1]hept-5-en-2-yl)-hex-5-enoate is obtained analogously to Example 5 (yield: 86%).

$^1$H-NMR(CDCl$_3$): δ = 5.95–6.32 (multiplet), 5.17–5.47 (multiplet) and 3.62 ppm (singlet).

EXAMPLE 7

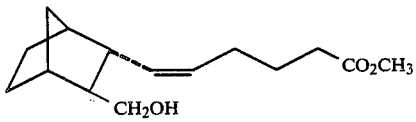

Methyl 6-(3-carboxybicyclo[2.2.1]hept-2-yl)-hex-5-enoate (a) A solution of 25.0 g (0.1 mole) of methyl 6-(3-hydroxymethyl-bicyclo[2.2.1]hept-2-yl)-hex-5-enoate in 60 ml of absolute dimethylformamide is added to 132.0 g (0.35 mole) of pyridinium dichromate in 200 ml of absolute dimethylformamide at 20° C. The reaction mixture is stirred at 20° C. for 9 hours, left to stand for 14 hours and then poured into 1.9 liters of water and extracted with diethyl ether. After drying over $Na_2SO_4$, the mixture is evaporated in vacuo and the residue is chromatographed on silica gel, using methylene chloride/methanol (95:5) to give 17.3 g of methyl 6-(3-carboxy-bicyclo-[2.2.1]hept-2-yl)-hex-5-enoate (yield: 65%)

$^1$H-NMR(CDCl$_3$): δ=10.9 (singlet), 5.13–5.53 (multiplet) and 3.70 ppm (singlet).

(b) 14.5 ml of Jones solution (26.7 g of chromium trioxide and 23 ml of concentrated $H_2SO_4$ made up to 100 ml with water) are allowed to run into a solution of 1.2 g (5 mmol) of methyl 6-(3-hydroxymethyl-bicyclo[2.2.1]hept-2-yl)-hex-5-enoate in 250 ml of absolute acetone at −20° C. The mixture is stirred at −20° C. for 3 hours and 40 ml of 2-propanol, followed by 30 ml of water, are then added and the pH is brought to 4 with solid $NaHCO_3$. The precipitate is decanted off, the solution is evaporated in vacuo and the residue is extracted 3 times with ethyl acetate. After the ethyl acetate phase has been dried over sodium sulphate, it is evaporated in vacuo and the methyl 6-(3-carboxybicyclo[2.2.1]hept-2-yl)-hex-5-enoate is purified as described under (a). 1.0 g (yield: 75%).

EXAMPLE 8

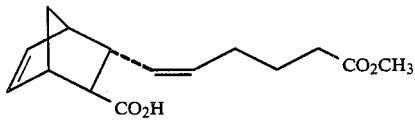

Methyl 6-(3-carboxy-bicyclo[2.2.1]hept-5-en-2-yl)-hex-5-enoate

Oxidation of methyl 6-(3-hydroxymethyl-bicyclo[2.2.1]hept-5-en-2-yl)-hex-5-enoate leads, as described in Example 7a, to methyl 6-(3-carboxy-bicyclo[2.2.1]hept-5-en-2-yl)-hex-5-enoate (yield: 59%)

$^1$H-NMR(CDCl$_3$): δ=11.16 (singlet), 5.93–6.40. (multiplet), 5.22–5.55 (multiplet) and 3.67 ppm (singlet)

EXAMPLE 9

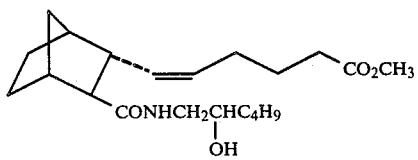

Methyl 6-[3-(N-2-hydroxy-hexyl)-carbamyl-bicyclo[2.2.1]-hept-2-yl]-hex-5-enoate 1.35 g (10 mmol) of N-hydroxybenzotriazole and then, at 0° C., 2.30 g (11 mmol) of dicyclohexylcarbodiimide are added to a solution of 2.66 g (10 mmol) of methyl 6-(3-carboxy-bicyclo[2.2.1]hept-2-yl)-hex-5-enoate in 10 ml of absolute tetrahydrofuran. The mixture is stirred at 0° C. for 1 hour and at 20° C. for 1 hour. Thereafter, 1.54 g (10 mmol) of 2-hydroxyhexylamine hydrochloride and 1.00 g (10 mmol) of triethylamine in 3 ml of absolute tetrahydrofuran are added and the mixture is stirred at 20° C. for 2 hours. The resulting precipitate is filtered off with suction and washed with tetrahydrofuran and the tetrahydrofuran solution is evaporated in vacuo. The evaporation residue is dissolved in 50 ml of ethyl acetate and the solution is washed successively with 10 ml of saturated aqueous sodium bicarbonate solution, 10 ml of 2N aqueous citric acid, 10 ml of saturated aqueous sodium bicarbonate solution and 10 ml of water and dried over sodium sulphate. The ethyl acetate is evaporated off in vacuo and the residue is chromatographed on silica gel using methylene chloride/methanol (95:5). 2.0 g (yield: 55%) of methyl 6-(3-(N-2-hydroxy-hexyl)-carbamyl-bicyclo[2.2.1]hept-2-yl)-hex-5-enoate are thus obtained.

IR (film): γ=1540, 1650 and 1740 cm$^{-1}$.

EXAMPLES 10–19

1 mole of an acid of the general formula (VIII) is reacted with 1 mole of the general formula (IX) analogously to Example 9 to give the reaction products listed in Table 2.

TABLE 2

Compounds prepared, of the general formula (I)

$$\text{bicyclo[2.2.1]hept-2-ene with } A-(CH_2)_n CO_2 R^1 \text{ and } CONHC(R^5)(R^6)-C(R^2)(R^3)(R^4)$$ (I)

| Example No. | $R^1$ | A | ⟨bicycle⟩ | $R^2$ | $R^3$ | $R^4$ | $R^5$ | $R^6$ | n | Yield (%) | Physical data $^1$H—NMR (CDCl$_3$) (ppm), IR (capsules) (cm$^{-1}$) |
|---|---|---|---|---|---|---|---|---|---|---|---|
| 10 | CH$_3$ | C≡C | norbornyl | H | cyclohexenyl | OH | H | H | 3 | 66 | 6.50 (~triplet), 5.60–5.83 (multiplet) |
| 11 | CH$_3$ | C≡C | norbornyl | CH$_3$ | C$_3$H$_7$ | OH | H | H | 3 | 81 | 3.66 (singlet), 1.13 (singlet) |
| 12 | CH$_3$ | C≡C | norbornyl | H | 3-Cl-phenyl | OH | H | H | 3 | 56 | 1730, 1530, 1645 |
| 13 | CH$_3$ | C≡C | norbornyl | CH$_3$ | phenyl | OH | H | H | 3 | 77 | 3.97 (doublet), 3.63 (singlet) |
| 14 | CH$_3$ | C≡C | norbornyl | CH$_3$ | phenyl | H | H | H | 3 | 82 | 1730, 1640, 1550 |
| 15 | CH$_3$ | C≡C | norbornyl | CH$_3$ | C$_3$H$_7$ | H | H | H | 3 | 76 | 5.63 (~triplet), 3.63 singlet) |
| 16 | CH$_3$ | C≡C | norbornyl | H | 3-Cl-phenyl | H | H | H | 3 | 83 | 6.93–7.33 (multiplet), 5.56 (~triplet) |
| 17 | CH$_3$ | C≡C | norbornenyl | H | C$_4$H$_9$ | OH | H | H | 3 | 77 | 1740, 1535, 1650 |
| 18 | CH$_3$ | C≡C | norbornenyl | CH$_3$ | C$_3$H$_7$ | OH | H | H | 3 | 64 | 5.96–6.47 (multiplet) 5.23–5.53 (multiplet) |
| 19 | CH$_3$ | C≡C | norbornenyl | H | 3-Cl-phenyl | OH | H | H | 3 | 81 | 3.60 (singlet) |

EXAMPLE 20

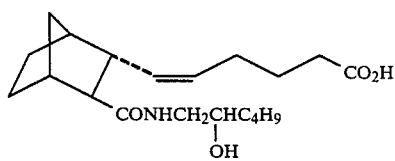

6-[3-(N-2-Hydroxy-hexyl)-carbamyl-bicyclo[2.2.1]hept-2-yl]-hex-5-enoic acid 3.65 g (10 mmol) of methyl 6-[3(N-2-hydroxyhexyl)-carbamyl-bicyclo[2.2.1]hept-2-yl]-hex-5-enoate are dissolved in 50 ml of methanol, and 10 ml of 1N NaOH and 6 ml of water are then added. The mixture is stirred at 20° C. for 12 hours and, after a further 12 hours, the reaction mixture is evaporated in vacuo, the evaporation residue is taken up in 100 ml of water and the mixture is acidified to pH 1 with 2N HCl and extracted 5 times with 50 ml of diethyl ether. After the organic phase has been dried over sodium sulphate, it is evaporated in vacuo and, if necessary, the residue is chromatographed on silica gel using methylene chloride/methanol (9:1). 2.46 g of 6-[3(N-2-hydroxy-hexyl)-carbamyl-bicyclo[2.2.1]-hept-2-yl]-hex-5-enoic acid are obtained (yield: 70%).

$^1$H-NMR(CDCl$_3$): δ=6.25 (∼triplet) and 0.88 ppm (∼triplet).

EXAMPLES 21–30

The amide-esters of the general formula (I) are hydrolyzed with the equivalent amount of 1N sodium hydroxide solution analogously to Example 20 to give the amide-acids (I) listed in Table 3.

Some amide-acids (I) already precipitate on acidification and can be isolated by filtration.

TABLE 3

Compounds prepared, of the general formula (I)

| Example No. | R$^1$ | A | R$^2$ | R$^3$ | R$^4$ | R$^5$ | R$^6$ | n | Yield (%) | Physical data $^1$H—NMR (CDCl$_3$) (ppm), IR (capsule or KBr) (cm$^{-1}$) |
|---|---|---|---|---|---|---|---|---|---|---|
| 21 | H | C=C | CH$_3$ | cyclohexenyl | OH | H | H | 3 | 73 | 5.53–5.87 (multiplet), 5.00–5.43 (multiplet) |
| 22 | H | C=C | CH$_3$ | C$_3$H$_7$ | OH | H | H | 3 | 73 | 1710, 1650, 1560 |
| 23 | H | C=C | H | 3-Cl-phenyl | OH | H | H | 3 | 89 | 6.10 (∼triplet), 4.67–4.90 (multiplet) |
| 24 | H | C=C | CH$_3$ | phenyl | OH | H | H | 3 | 79 | 5.08–5.32 (multiplet), 1.50 (singlet) |
| 25 | H | C=C | CH$_3$ | phenyl | H | H | H | 3 | 85 | 5.60 (∼triplet) |
| 26 | H | C=C | CH$_3$ | C$_3$H$_7$ | H | H | H | 3 | 91 | 5.71 (∼triplet), 9.47 (singlet) |
| 27 | H | C=C | H | 3-Cl-phenyl | H | H | H | 3 | 88 | 7.02–7.25 (multiplet), 5.62 (∼triplet) |
| 28 | H | C=C | H | C$_4$H$_9$ | OH | H | H | 3 | 71 | 1710, 1650, 1540 |
| 29 | H | C=C | CH$_3$ | C$_3$H$_7$ | OH | H | H | 3 | 76 | 1.10 (singlet) |
| 30 | H | C=C | H | 3-Cl-phenyl | OH | H | H | 3 | 88 | 5.83–6.57 (multiplet) 5.17–5.57 (multiplet) |

EXAMPLE 31

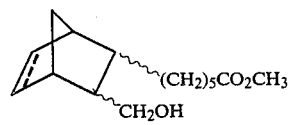

Methyl 6-(3-hydroxymethyl-bicyclo[2.2.1]hept-2-yl)-hexanoate (a) 28.7 g (0.11 mole) of methyl 6-(3-hydroxymethyl-bicyclo[2.2.1]hept-2-yl)-hex-2-enoate are hydrogenated in 450 ml of methanol, with the addition of 12 g of palladium-on-charcoal (5% strength), at 60° C. under a pressure of 30 bar for 1½ hours. The catalyst is removed by filtration, the methanol is evaporated off in vacuo and the oil which remains is chromatographed on silica gel, using methylene chloride/methanol (99:1), to give 25.5 g (91% yield) of methyl 6-(3-hydroxymethyl-bicyclo[2.2.1]hept-2-yl)-hexanoate.

$^1$H-NMR(CDCl$_3$): δ=3.63 ppm (singlet)

(b) Methyl 6-(3-hydroxymethyl-bicyclo[2.2.1]hept-2-yl)-hexanoate is obtained in 77% yield from methyl 6-(3-hydroxymethyl-bicyclo[2.2.1]hept-5-en-2-yl)-hex-2-enoate analogously to Example 31a.

EXAMPLE 32

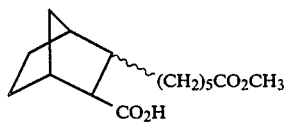

Methyl 6-(3-carboxy-bicyclo[2.2.1]hept-2-yl)-hexanoate

Methyl 6-(3-carboxy-bicyclo[2.2.1]-hexanoate is obtained in 61% yield from methyl 6-(3-hydroxymethyl-bicyclo[2.2.1]hept-2-yl)-hexanoate by the process described in Example 7a. IR (film): δ=1710 and 1730 cm$^{-1}$.

EXAMPLES 33–38

The amide-esters and amide-acids of the general formula (I) listed in Table 4 are obtained as described in Example 9 or Example 20.

TABLE 4:

Compounds prepared, of the general formula (I)

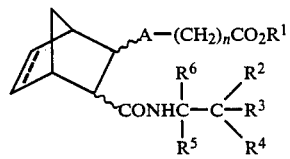

(I)

| Example No. | R$^1$ | n | A | R$^2$ | R$^3$ | R$^4$ | R$^5$ | R$^6$ | Yield (%) | Physical data $^1$H—NMR (CDCl$_3$) (ppm), IR (capsules) (cm$^{-1}$) |
|---|---|---|---|---|---|---|---|---|---|---|
| 33 | CH$_3$ | 3 | CH$_2$CH$_2$ | (norbornyl-CH$_3$) | (phenyl) | H | H | H | 82 | 5.42 (~triplet), 3.65 (singlet) |
| 34 | CH$_3$ | 3 | CH$_2$CH$_2$ | (norbornyl-CH$_3$) | C$_3$H$_7$ | H | H | H | 76 | 1730, 1640, 1530 |
| 35 | CH$_3$ | 3 | CH$_2$CH$_2$ | (norbornyl-H) | (chlorophenyl) | H | H | H | 83 | 6.97–7.33 (multiplet), 3.63 (singlet), |
| 36 | H | 3 | CH$_2$CH$_2$ | (norbornyl-CH$_3$) | (phenyl) | H | H | H | 85 | 1710, 1640, 1530 |
| 37 | H | 3 | CH$_2$CH$_2$ | (norbornyl-CH$_3$) | C$_3$H$_7$ | H | H | H | 91 | 9.50 (singlet) 5.71 (~triplet) |

TABLE 4:-continued

Compounds prepared, of the general formula (I)

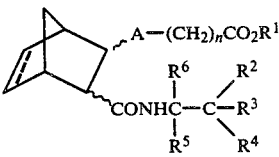

(I)

| Example No. | R¹ | n | A |  | R² | R³ | R⁴ | R⁵ | R⁶ | Yield (%) | Physical data $^1$H—NMR (CDCl$_3$) (ppm), IR (capsules) (cm$^{-1}$) |
|---|---|---|---|---|---|---|---|---|---|---|---|
| 38 | H | 3 | CH₂CH₂ | 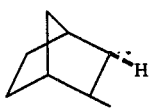 | 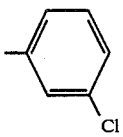 | | H | H | H | 88 | 8.11 (singlet), 5.62 (~triplet) |

It will be understood that the specification and examples are illustrative but not limitative of the present invention and that other embodiments within the spirit and scope of the invention will suggest themselves to those skilled in the art.

We claim:

1. A norbornane- or norbornene-carboxylic acid amide of the general formula

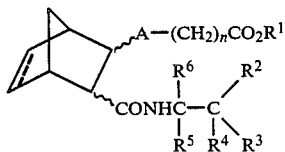

in which

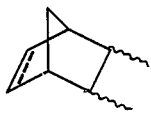

represents the part structure

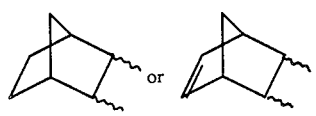

A represents a

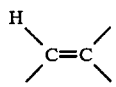

or —CH₂—CH₂— group,

R¹ and R² each independently is hydrogen or an alkyl radical with 1-6 carbon atoms, R³ is alkyl or alkenyl which has 1-8 carbon atoms and is optionally substituted by halogen or alkyl with 1 or 2 carbon atoms, cycloalkyl or cycloalkeny with 3 to 7 carbon atoms, an aromatic radical which has 6 or 10 carbon atoms and and is optionally substituted by halogen, by alkyl with 1 or 2 carbon atoms or by halogenoalkyl with 1 or 2 carbon atoms, or is pyridyl, imidazolyl, furyl or thionyl, R⁴ is hydrogen or a hydroxyl group, R⁵ and R⁶ each independently is hydrogen or alkyl with 1 to 4 carbon atoms, and n is a number from 2 to 6, and, if R¹ is hydrogen, also a physiologically acceptable salt thereof.

2. A compound or salt according to claim 1, in which R² is hydrogen or alkyl with 1 to 4 carbon atoms, R³ is alkyl or alkenyl with 1 to 6 carbon atoms, cycloalkyl or cycloalkenyl with 5 or 6 carbon atoms, phenyl optionally substituted by halogen, methyl, ethyl, halomethyl or haloethyl, or is pyridyl, imidazolyl, furyl or thienyl, R⁵ and R⁶ each independently is hydrogen or alkyl with 1 to 3 carbon atoms, and n is a number from 2 to 4.

3. A compound or salt according to claim 1, in which R² is hydrogen or methyl,

R³ is propyl, butyl, pentyl, cyclopentyl, cyclohexyl, cyclohexenyl, phenyl, phenyl which is substituted by chlorine or trifluoromethyl, pyridyl or imidazolyl.

R⁵ and R⁶ are hydrogen, and n is a number from 2 to 4.

4. A compound according to claim 1, wherein such compound is 6-[3-(N-2-hydroxy-hexyl)-carbamylbicyclo[2.2.1]-hept-2-yl]-hex-5-enoic acid or a physiologically acceptable salt thereof.

5. A compound according to claim 1, wherein such compound is 6-[3-(N-2-(cyclohex-3-enyl)-2-hydroxyethyl)carbamyl-bicyclo[2.2.1]-hept-2-yl]-hex-5-enoic acid or a physiologically acceptable salt thereof.

6. A compound according to claim 1, wherein such compound is 6-[3-(N-2-m-chlorophenyl-2-hydroxyethyl)-carbamyl-bicyclo[2.2.1]-hept-2-yl]-hex-5-enoic acid or a physiologically acceptable salt thereof.

7. A compound according to claim 1, wherein such compound is 6-[3-(N-2-hydroxy-2-phenyl-propyl)-carbamyl-bicyclo[2.2.1]-hept-2-yl]-hex-5-enoic acid or a physiologically acceptable salt thereof.

8. A compound according to claim 1, wherein such compound is 6-[3-(N-2-m-chlorophenyl-2-hydroxyethyl)-carbamyl-bicyclo[2.2.1]-hept-5-en-2-yl]-hex-5-enoic acid or a physiologically acceptable salt thereof.

9. A thromboxan antagonistic composition comprising an amount effective therefor of a compound or salt according to claim 1 in admixture with a diluent.

10. A unit dose of a composition according to claim 9 in the form of a tablet, capsule or ampule.

11. A method of antagonizing thromboxan in a patient which comprises administering to such patient a thromboxan-antagonizing effective amount of a compound or salt according to claim 1.

12. The method according to claim 11, wherein such compound is
6-[3-(N-2-hydroxy-hexyl)-carbamyl-bicyclo[2.2.1]-hept-2-yl]-hex-5-enoic acid,
6-[3-(N-2-(cylohex-3-enyl)-2-hydroxy-ethyl)-carbamyl-bicyclo[2.2.1]-hept-2-yl]-hex-5-enoic acid,
6-[3-(N-2-m-chlorophenyl-2-hydroxy-ethyl)-carbamyl-bicyclo[2.2.1]-hept-2-yl]-hex-5-enoic acid,
6-[3-(N-2-hydroxy-2-phenyl-propyl)-carbamyl-bicyclo[2.2.1]-hept-2-yl]-hex-5-enoic acid or
6-[3-(N-2-m-chlorophenyl-2-hydroxy-ethyl)-carbamyl-bicyclo[2.2.1]-hept-5-en-2-yl]-hex-5-enoic acid,
or a physiologically acceptable salt thereof.

* * * * *

UNITED STATES PATENT AND TRADEMARK OFFICE
CERTIFICATE OF CORRECTION

PATENT NO. : 4,622,339

DATED : Nov. 11, 1986

INVENTOR(S) : Folker Lieb, et al.

Page 1 of 3

It is certified that error appears in the above-identified patent and that said Letters Patent is hereby corrected as shown below:

| | |
|---|---|
| Title Page, under "U.S. Patent Documents", line 1 | Delete "MohrbacKer" and substitute --Mohrbacher-- |
| Abstract, line 15 | Correct spelling of "with" |
| Col. 2, line 40 | End of formula delete "O\O" and substitute --O\O/O-- |
| Col. 2, line 48 | Delete formula and substitute -- [structure] -- |
| Col. 2, line 65 | Delete end of formula and substitute -- [structure with OH] -- |
| Col. 4, line 62 | Delete formula and substitute -- [structure] -- |
| Col. 6, line 5 | End of formula delete "dichloromate" and substitute --dichromate-- |
| Col. 11, line 53 | Correct spelling of --clinical-- |
| Col. 14, line 55 | End of formula delete "$\sim CO_2H$" and substitute --$\sim CO_2CH_3$-- |

UNITED STATES PATENT AND TRADEMARK OFFICE
CERTIFICATE OF CORRECTION

PATENT NO. : 4,622,339
DATED : Nov. 11, 1986
INVENTOR(S) : Folker Lieb, et al.

It is certified that error appears in the above-identified patent and that said Letters Patent is hereby corrected as shown below:

| | |
|---|---|
| Col. 16, line 65 | After "mole of" insert --amine of-- |
| Cols. 17-18, Table 2, Example No. 14, last column | Delete "1550" and substitute --1530-- |
| Cols. 17-18, Table 2, Example Nos. 17, 18, and 19, third column | Insert --↳-- bottom of formula and follows |
| Col. 20, Table 3, Example Nos. 28, 29 and 30 | Delete bottom of formula as follows: "⌐" and substitute -- ⌐ -- |
| Col. 20, line 65 | In formula delete " ~~ " and substitute -- ˋˋˋ -- |
| Col. 20, line 65 | Delete beginning of formula and substitute -- △ -- |
| Col. 22, line 5 | In formula delete " ⁀ " and substitute -- ˋˋ -- |
| Cols. 22 and 23, Table 4, 5th column heading | Delete formula and substitute -- ▱ -- |

UNITED STATES PATENT AND TRADEMARK OFFICE
CERTIFICATE OF CORRECTION

PATENT NO. : 4,622,339                    Page 3 of 3

DATED    : Nov. 11, 1986

INVENTOR(S) : Folker Lieb, et al.

It is certified that error appears in the above-identified patent and that said Letters Patent is hereby corrected as shown below:

| | |
|---|---|
| Col. 22, Table 4, Example No. 33, last column | Delete "5.42" and substitute --5.45-- |
| Col. 24, line 26 | Delete "thionyl" and substitute --thienyl-- |
| Col. 24, lines 52, 53 | Delete "carbamylbicyclo" and substitute --carbamyl-bicyclo-- |

Signed and Sealed this

Fourteenth Day of April, 1987

Attest:

DONALD J. QUIGG

Attesting Officer

Commissioner of Patents and Trademarks